OAK TREE
Filed Oct. 23, 1973 3 Sheets-Sheet 1
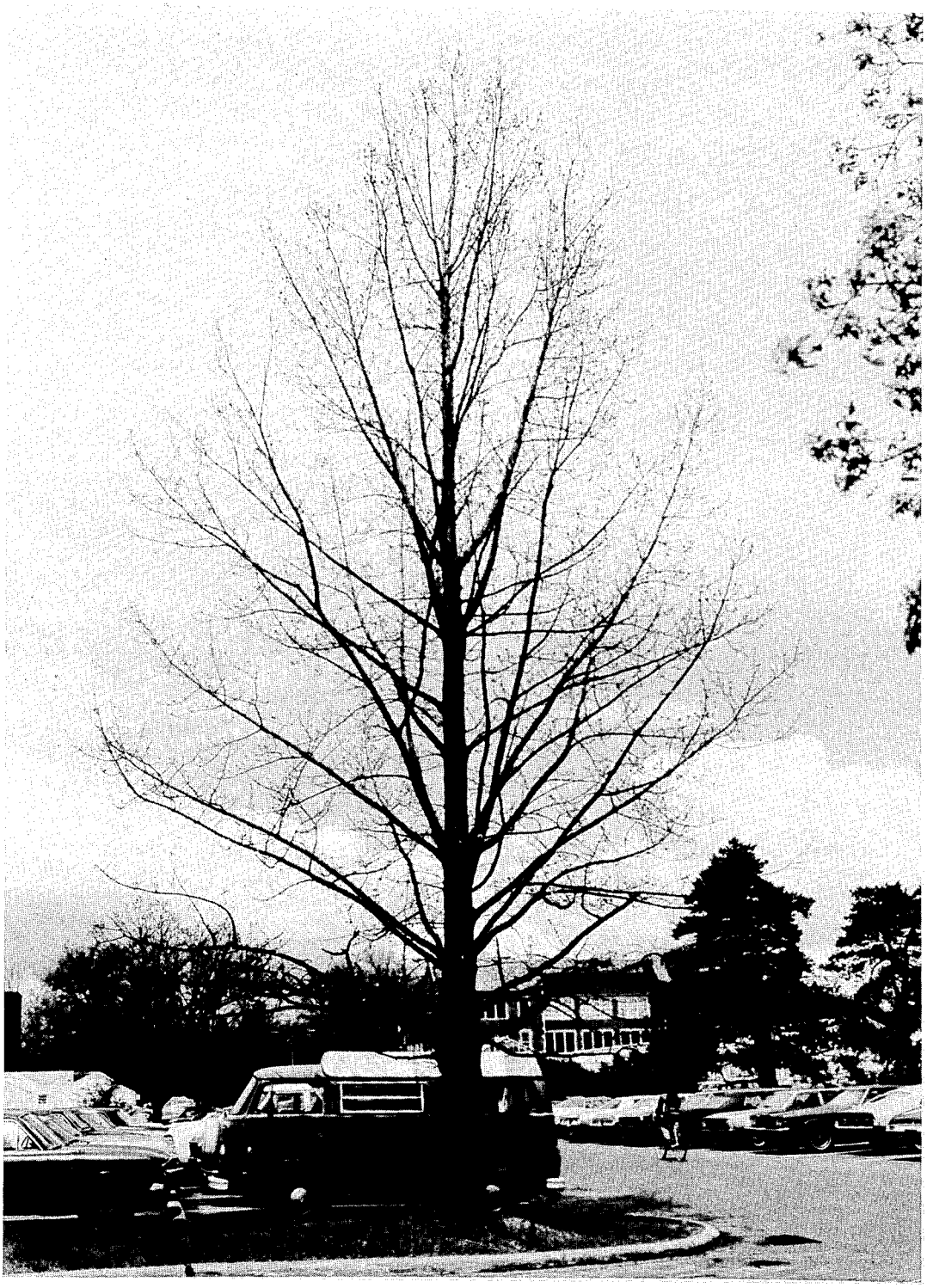

OAK TREE
Filed Oct. 23, 1973 3 Sheets-Sheet 2
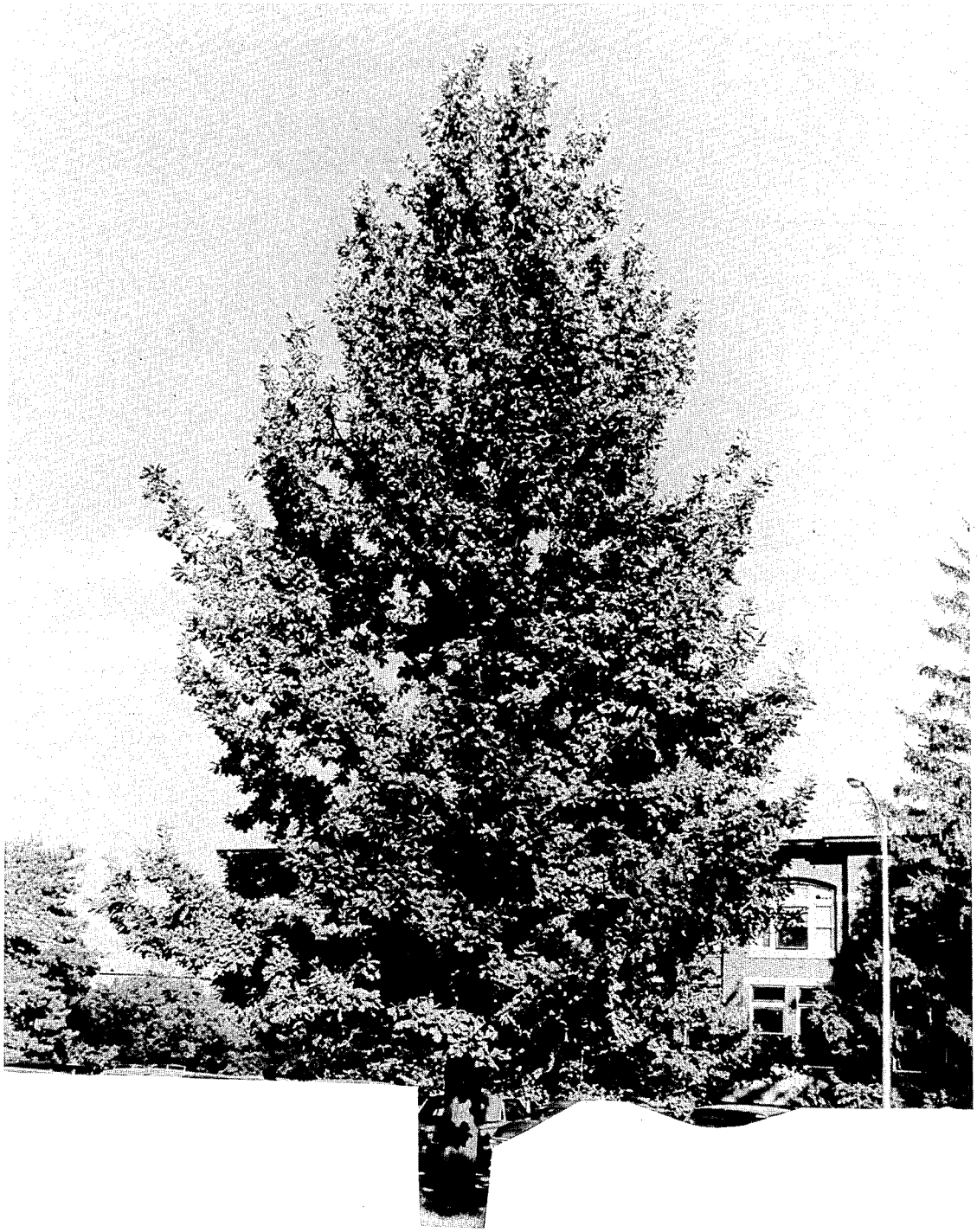

OAK TREE
Filed Oct. 23, 1973 3 Sheets-Sheet 3
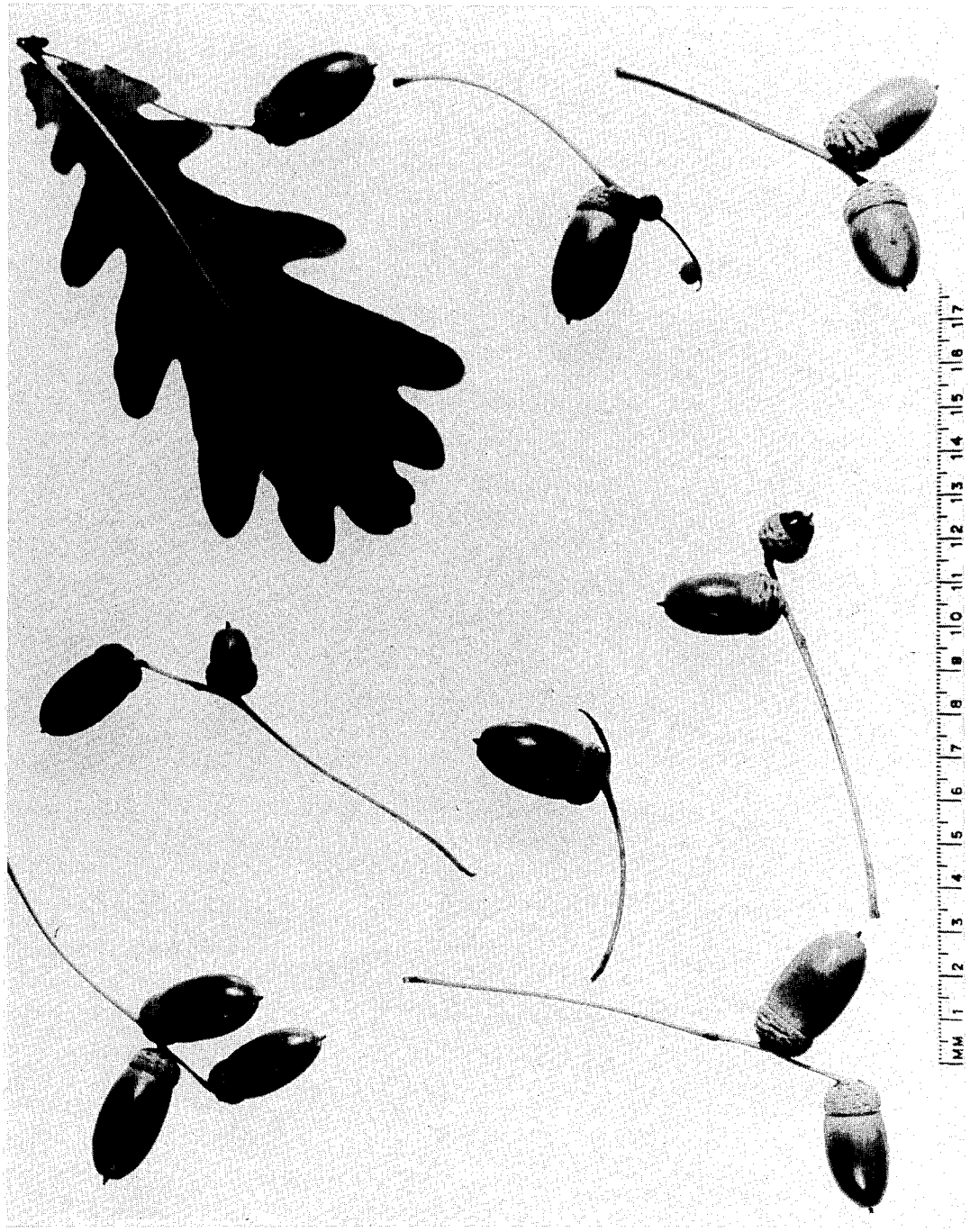

United States Patent

Plant Pat. 3,707

Patented Apr. 22, 1975

3,707

OAK TREE

Milton Baron, Haslett, Mich., assignor to J. Frank Schmidt and Son Co., Troutdale, Oreg.

Filed Oct. 23, 1973, Ser. No. 408,829

Int. Cl. A01h 5/12

U.S. Cl. Plt.—51 1 Claim

The present invention relates to a new and distinct variety of English oak tree of the species botanically known as *Quercus robur,* which was discovered and developed by me as a selected cultivated seedling of unknown parentage, among a group of plants of this species being grown under my supervision and control at Michigan State University at East Lansing, Mich.

Over many years, the University has collected or received by gift, or otherwise reproduced, many seedling shade trees, and the present new English oak seedling, among hundreds of others (many grown from acorns produced thereby), have been undergoing tests and experimental developments in the University Campus Nursery and on the campus grounds at East Lansing since 1946. When the Dutch Elm Disease (DED) became epidemic in this area starting about 1961, these English oak seedlings were even more closely scrutinized as likely substitutes for American elms. Over this extended period of observations, four salient traits bearing on the overall landscape suitability of the English oak have emerged:

A. Ease of transplanting in late winter or spring;
B. Low maintenance qualities as manifested by
   (a) exceptional ability to withstand severe environmental stress resulting from compacted soil, restricted root run, extended drought, gale winds and ice storms;
   (b) absence of any need over a period of nearly three decades to initiate programs to control insects or disease;
C. Long-persisting foliage casting effective shade until late October (and later farther south); and
D. Pronounced variability in form and growth rate, the latter varying 300% from about 6 inches to over 18 inches annually.

The first three of these traits (A, B, and C) qualify the English oak (including the instant variety) as a prime candidate for urban plantings requiring many individuals of one kind, such as boulevard and street plantings.

The fourth trait (D) in equally decisive fashion precludes the English oak from assuming its rightful place among the finest of trees for urban planting when grown from seeds (acorns). Because of its notorious variability, it simply cannot be recommended for any use where landscape specifications demand uniform crown proportions and growth rate in order to achieve integrated landscape design. Furthermore, this variability is evident even among seedling progeny from a single seed parent, as demonstrated by marked differences in growth rate observed among 9,000 two-year old seedlings grown by me from a single high-producing campus tree in 1964.

Finally, seedlings grown from acorns produced within the range of our native *A. alba* and *Q. macrocarpa* have the potential for an even wider range of variability as illustrated by several putative hybrids that have also been grown by me on the University campus aforesaid.

Clearly then, the English oak cannot fulfill its great promise in the absence of asexual propagation. Such propagation of a superior selected variety, tailored to perform a specific landscape role, and made economically feasible by patent protection, constitutes a first step in converting the notorious variability of this species from a handicap to a virtue. Vegetative propagation of the subject variety makes available an ecologically and esthetically sound candidate for any landscape application calling for a tree having a relatively narrow crown and strong central leader.

As the result of my prolonged observations and tests, I am convinced that the selected seedling which is the subject hereof is definitely a new and distinct variety, as particularly evidenced by the following unique combination of primary characteristics which are outstanding therein and which distinguish the same from all other varieties of English oak trees of which I am aware:

(1) A narrow pyramidal crown, with a height/width ratio of 1.52, resulting from activity of an unusually strong leader, together with lateral branches less widely diverging (averaging 31° from the vertical) than is typical of the species;
(2) Exceptional crotch strength from a crown so narrow, which is the result of branches which arch sharply upward from a relatively wide crotch angle of about 55°;
(3) Light fruit production, in most years amounting to only a few dozen acorns; and
(4) Ideal suitability for use where the landscape requires a relatively narrow crown with a strong central leader.

The only superficially similar form of English oak known to me is *Q.r.* "Fastigiata," but there are several fundamental differences. The 1.5 height/width ratio of the subject seedling is at considerable variance with the 2.7 determined for a typical *Q.r.* "Fastigiata" specimen of comparable age. Moreover, the subject seedling is broadest at the base while "Fastigiata" is broadest near the middle. Even more significant differences are to be found in the internal crown structure. While in the instant seedling the trunk and central leader is clearly distinguishable to the very tip of the crown, in "Fastigiata" the trunk divides in the lower third of the crown into a dozen or more wand-like branches of nearly equal rank. Furthermore, the crotches of these lengthy branches diverge at a very narrow angle of only about 5°, with the result that cumulative production of annual rings of wood on branch and trunk act as an ever-thickening wedge tending to force open the crotch and thereby gradually increasing crown width as well as leverage exerted on the crotch by the elongated branch. In contrast, the subject seedling with its relatively wide crotch angle and short scaffold branches associated with strong trunk development presages minimum crotch failure from such wedge action and pull of gravity.

In the light of the significant differences noted above, it is evident that asexual progeny of the subject seedling have lower maintenance requirements and greater longevity, while sacrificing nothing in the way of esthetic quality.

Asexual reproduction of my new seedling by soft budding on potted 2-year seedlings, as performed under my direction and supervision at the Beaumont Nursery of Michigan State University, shows that the foregoing characteristics and distinctions come true and are established and transmitted through succeeding propagations.

The accompanying drawings show typical mature tree specimens of my new English oak variety while in foliage as well as bare of foliage, and also a typical specimen leaf and typical specimens of the fruit (acorns).

The following is a detailed description of the new variety, with color terminology in accordance with general color terms of ordinary dictionary significance, since the color features are not materially significant or different from those normal to the species:

A large narrow-pyramidal tree with a crown height/width ratio of about 1.5 and a long, well-defined trunk; crotches diverging from the trunk at an angle of about 55°, with the angle of branch ascent shortly narrowing to an average of about 31°; dark bark, deeply furrowed, forming irregular plates; twigs glabrous, with those of the second year gray-brown and of the first year greenish brown; buds sparsely villous, with the terminal clearly 5-angled, and the lateral divergent and nearly terete; leaves glabrous, with the blade rather thin, medium green above and pale blue-green below, obviate, mostly about 15–18 (13.5–20) cm. long and about 8–10 (7.1–13.6) cm. wide, pinnately lobed, with 5–7 pairs of rounded lobes separated by rounded or pointed sinuses extending more than half-way to the midrib, base inequilateral, falcate ears symmetrical and typically clasping the 5–10 mm. long petiole; fruits sparsely produced, borne in small clusters of 1–3 (averaging less than 2) on a relatively slender peduncle 1.2 mm. in diameter and 5–7 (4.9–8.7) cm. long, with the acorns being lustrous brown, long ellipsoid, about 2.8 (2.6–3.0) cm. long and 1.5 cm. in diameter; cut thin-walled, deep bowl-shaped, covering about ⅙ of the acorn, and being about 7 mm. deep and 1.4 cm. in diameter, with the outer surface smooth except for the scarious free tips of the thin glabrous scales.

I claim:

1. A new and distinct variety of English oak tree of the species botanically known as *Quercus robur*, substantially as herein shown and described, characterized particularly as to novelty by the unique combination of a narrow pyramidal crown, with a height/width ratio of 1.52, resulting from activity of an unusually strong leader, together with lateral branches less widely diverging (averaging 31° from the vertical) than is typical of the species; exceptional crotch strength from a crown so narrow, which is the result of branches which arch sharply upward from a relatively wide crotch angle of about 55°; light fruit production, in most years amounting to only a few dozen acorns; and ideal suitability for use where the landscape requires a relatively narrow crown with a strong central leader.

References Cited

New Illustrated Encyclopedia of Gardening, Everett, 1960, Greystone Press, pp. 1748–9 relied on.

ROBERT E. BAGWILL, Primary Examiner